United States Patent
Ichim et al.

(10) Patent No.: US 11,759,495 B2
(45) Date of Patent: Sep. 19, 2023

(54) UPREGULATION OF THERAPEUTIC T REGULATORY CELLS AND SUPPRESSION OF SUICIDAL IDEATIONS IN RESPONSE TO INFLAMMATION BY ADMINISTRATION OF NUTRACEUTICAL COMPOSITIONS ALONE OR COMBINED WITH MINOCYCLINE

(71) Applicant: Therapeutic Solutions International, Inc., Oceanside, CA (US)

(72) Inventors: Thomas E. Ichim, Oceanside, CA (US); Timothy G. Dixon, Oceanside, CA (US); Kalina O'Connor, Oceanside, CA (US)

(73) Assignee: Therapeutic Solutions International, Inc., Oceanside, CA (US)

( * ) Notice: Subject to any disclaimer, the term of this patent is extended or adjusted under 35 U.S.C. 154(b) by 0 days.

(21) Appl. No.: 17/461,486

(22) Filed: Aug. 30, 2021

(65) Prior Publication Data
US 2022/0062367 A1    Mar. 3, 2022

Related U.S. Application Data (60) Provisional application No. 63/071,381, filed on Aug. 28, 2020.

(51) Int. Cl.
| | | |
|---|---|---|
| A61K 36/82 | (2006.01) |
| A61K 36/45 | (2006.01) |
| A61K 31/65 | (2006.01) |
| A61K 36/31 | (2006.01) |
| A61K 36/71 | (2006.01) |

(52) U.S. Cl.
CPC ............ *A61K 36/82* (2013.01); *A61K 31/65* (2013.01); *A61K 36/31* (2013.01); *A61K 36/45* (2013.01); *A61K 36/71* (2013.01)

(58) Field of Classification Search
CPC ........ A61K 31/65; A61K 36/31; A61K 36/45; A61K 36/71; A61K 36/82
See application file for complete search history.

(56) References Cited

U.S. PATENT DOCUMENTS 11,229,674 B1 * 1/2022 Ichim ................... A61P 29/00

* cited by examiner

*Primary Examiner* — Aaron J Kosar
(74) *Attorney, Agent, or Firm* — Baumgartner Patent Law; Marc Baumgartner (57) ABSTRACT

Disclosed are compositions of matter, treatments and protocols useful for induction of T regulatory cells in response to inflammation, as well as inhibition of suicidal ideations and/or neuroinflammation. In some embodiments the invention teaches the administration of a therapeutic combination of ingredients comprising of minocycline, pterostilbene, *Nigella sativa*, sulforaphane, and epigallocatechin-3-gallate (EGCG) to a mammal undergoing upregulation of inflammatory mediators. In another embodiment, the invention teaches administration of said therapeutic combination to a mammal infected with said SARS-CoV-2 and/or possessing suicidal ideations. In some embodiments dosage of said therapeutic combination is based on inflammatory and/or immunological parameters observed in patients.

19 Claims, 3 Drawing Sheets

UPREGULATION OF THERAPEUTIC T REGULATORY CELLS AND SUPPRESSION OF SUICIDAL IDEATIONS IN RESPONSE TO INFLAMMATION BY ADMINISTRATION OF NUTRACEUTICAL COMPOSITIONS ALONE OR COMBINED WITH MINOCYCLINE

CROSS-REFERENCE TO RELATED APPLICATIONS

This application claims priority to U.S. Provisional Application No. 63/071,381, filed Aug. 28, 2020, which is incorporated herein by reference in its entirety.

FIELD OF THE INVENTION

The invention relates to the field of treating suicidal ideations with nutraceutical compositions alone or in combination with Minocycline.

BACKGROUND OF THE INVENTION

T regulatory cells (Treg) play a fundamental role in protecting the body from autoimmunity. The use of Treg cells has been shown effective in models of autoimmune conditions including type 1 diabetes [1-10], rheumatoid arthritis [11], and multiple sclerosis [12]. The induction of Treg cells occurs through thymic mechanisms during development of the immune system, these are called natural Tregs and in the periphery, they are called inducible Tregs. There is a need to develop new means of stimulating Tregs.

SUMMARY

Preferred embodiments are directed to methods of stimulating production of T regulatory cells in a mammal comprising the steps of: a) selecting a mammal in need of therapy; b) administering to said mammal a therapeutic combination comprising of: a) Green Tea and/or extract thereof, b) Blueberry and/or extract thereof, c) *Nigella Sativa* and/or extract thereof; d) broccoli and/or extract thereof and e) minocycline.

Preferred methods include embodiments wherein said green tea extract is epigallocatechin-3-gallate or an analogue thereof.

Preferred methods include embodiments wherein said blueberry extract is pterostilbene or an analogue thereof.

Preferred methods include embodiments wherein said *Nigella Sativa* extract is thymoquinone or an analogue thereof.

Preferred methods include embodiments wherein said broccoli extract is sulforaphane or an analogue thereof.

Preferred methods include embodiments wherein said mammal in need of therapy is a human.

Preferred methods include embodiments wherein said human suffers from a condition associated with enhanced inflammation.

Preferred methods include embodiments wherein said enhanced inflammation is an increase of interleukin-1 beta concentration in blood of 25% or more as compared to an age-matched individual.

Preferred methods include embodiments wherein said enhanced inflammation is an increase of TNF-alpha concentration in blood of 25% or more as compared to an age-matched individual.

Preferred methods include embodiments wherein said enhanced inflammation is an increase of interleukin-6 concentration in blood of 25% or more as compared to an age-matched individual.

Preferred methods include embodiments wherein said enhanced inflammation is an increase of interleukin-8 concentration in blood of 25% or more as compared to an age-matched individual.

Preferred methods include embodiments wherein said enhanced inflammation is an increase of interleukin-11 concentration in blood of 25% or more as compared to an age-matched individual.

Preferred methods include embodiments wherein said enhanced inflammation is an increase of interleukin-12 concentration in blood of 25% or more as compared to an age-matched individual.

Preferred methods include embodiments wherein said enhanced inflammation is an increase of interleukin-15 concentration in blood of 25% or more as compared to an age-matched individual.

Preferred methods include embodiments wherein said enhanced inflammation is an increase of interleukin-17 concentration in blood of 25% or more as compared to an age-matched individual.

Preferred methods include embodiments wherein said enhanced inflammation is an increase of interleukin-18 concentration in blood of 25% or more as compared to an age-matched individual.

Preferred methods include embodiments wherein said enhanced inflammation is an increase of interleukin-21 concentration in blood of 25% or more as compared to an age-matched individual.

Preferred methods include embodiments wherein said enhanced inflammation is an increase of interleukin-23 concentration in blood of 25% or more as compared to an age-matched individual.

Preferred methods include embodiments wherein said enhanced inflammation is an increase of interleukin-27 concentration in blood of 25% or more as compared to an age-matched individual.

Preferred methods include embodiments wherein said enhanced inflammation is an increase of interleukin-33 concentration in blood of 25% or more as compared to an age-matched individual.

Preferred methods include embodiments wherein said enhanced inflammation is an increase of HMGB1 concentration in blood of 25% or more as compared to an age-matched individual.

Preferred methods include embodiments wherein said enhanced inflammation is an increase of interferon alpha concentration in blood of 25% or more as compared to an age-matched individual.

Preferred methods include embodiments wherein said enhanced inflammation is an increase of interferon beta concentration in blood of 25% or more as compared to an age-matched individual.

Preferred methods include embodiments wherein said enhanced inflammation is an increase of interferon gamma concentration in blood of 25% or more as compared to an age-matched individual.

Preferred methods include embodiments wherein said enhanced inflammation is a decrease of interleukin-4 concentration in blood of 25% or more as compared to an age-matched individual.

Preferred methods include embodiments wherein said enhanced inflammation is a decrease of interleukin-10 concentration in blood of 25% or more as compared to an age-matched individual.

Preferred methods include embodiments wherein said enhanced inflammation is a decrease of interleukin-13 concentration in blood of 25% or more as compared to an age-matched individual.

Preferred methods include embodiments wherein said enhanced inflammation is a decrease of interleukin-20 concentration in blood of 25% or more as compared to an age-matched individual.

Preferred methods include embodiments wherein said enhanced inflammation is a decrease of interleukin-35 concentration in blood of 25% or more as compared to an age-matched individual.

Preferred methods include embodiments wherein said enhanced inflammation is a decrease of HLA-G concentration in blood of 25% or more as compared to an age-matched individual.

Preferred methods include embodiments wherein said enhanced inflammation is a decrease of TGF-beta concentration in blood of 25% or more as compared to an age-matched individual.

Preferred methods include embodiments wherein said enhanced inflammation is a decrease of PGE-2 concentration in blood of 25% or more as compared to an age-matched individual.

Preferred methods include embodiments wherein said human in need of therapy suffers from suicidal ideations.

Preferred methods include embodiments wherein said human in need of therapy suffers from depression.

Preferred methods include embodiments wherein said person has an elevated risk of suicide.

Preferred methods include embodiments wherein elevated risk of suicide is determined by the SAD PERSONS Scale.

Preferred methods include embodiments wherein said elevated risk of suicide is determined by the SAD PERSONS Scale.

Preferred methods include embodiments wherein said elevated risk of suicide is determined by the Manchester Self-Harm Rule (MSHR).

Preferred methods include embodiments wherein said elevated risk of suicide is determined by the Sodersjukhuset Self Harm Rule Preferred methods include embodiments wherein said elevated risk of suicide is determined by the Beck Hopelessness Scale.

Preferred methods include embodiments wherein said T regulatory cells express FoxP3.

Preferred methods include embodiments wherein said T regulatory cells express membrane bound TGF-beta.

Preferred methods include embodiments wherein said T regulatory cells express HLA-G.

Preferred methods include embodiments wherein said T regulatory cells produce interleukin-10.

Preferred methods include embodiments wherein said T regulatory cells produce interleukin-1 receptor antagonist.

Preferred methods include embodiments wherein said T regulatory cells produce vasoactive intestinal peptide.

Preferred methods include embodiments wherein said T regulatory cells produce IL-4.

Preferred methods include embodiments wherein said T regulatory cells produce IL-13.

Preferred methods include embodiments wherein said T regulatory cells produce IL-20.

Preferred methods include embodiments wherein said T regulatory cells produce IL-35.

Preferred methods include embodiments wherein said T regulatory cells express CD4.

Preferred methods include embodiments wherein said T regulatory cells express CD25.

Preferred methods include embodiments wherein said T regulatory cells express Fas ligand.

Preferred methods include embodiments wherein said T regulatory cells express CTLA-4.

Preferred methods include embodiments wherein said T regulatory cells express GITR-ligand.

Preferred methods include embodiments wherein said T regulatory cells express PD-1 ligand.

Preferred methods include embodiments wherein said T regulatory cells express Helios.

Preferred methods include embodiments wherein said T regulatory cells express CD40 ligand.

Preferred methods include embodiments wherein said T regulatory cells express CD47.

Preferred methods include embodiments wherein said T regulatory cells express CD3.

Preferred methods include embodiments wherein said T regulatory cells express CD105.

Preferred methods include embodiments wherein said T regulatory cells express CD28.

Preferred methods include embodiments wherein said T regulatory cells express CD18.

Preferred methods include embodiments wherein said T regulatory cells suppress dendritic cell maturation.

Preferred methods include embodiments wherein said suppression of dendritic cell maturation implies resistance of dendritic cells to responding to a maturation agent.

Preferred methods include embodiments wherein said responding to said maturation agent implies augmentation of MHC I expression.

Preferred methods include embodiments wherein said responding to said maturation agent implies augmentation of MHC II expression.

Preferred methods include embodiments wherein said responding to said maturation agent implies augmentation of CD40 expression.

Preferred methods include embodiments wherein said responding to said maturation agent implies augmentation of CD80 expression.

Preferred methods include embodiments wherein said responding to said maturation agent implies augmentation of CD86 expression.

Preferred methods include embodiments wherein said responding to said maturation agent implies augmentation of IL-12 expression.

DETAILED DESCRIPTION OF THE INVENTION

Figure 1:
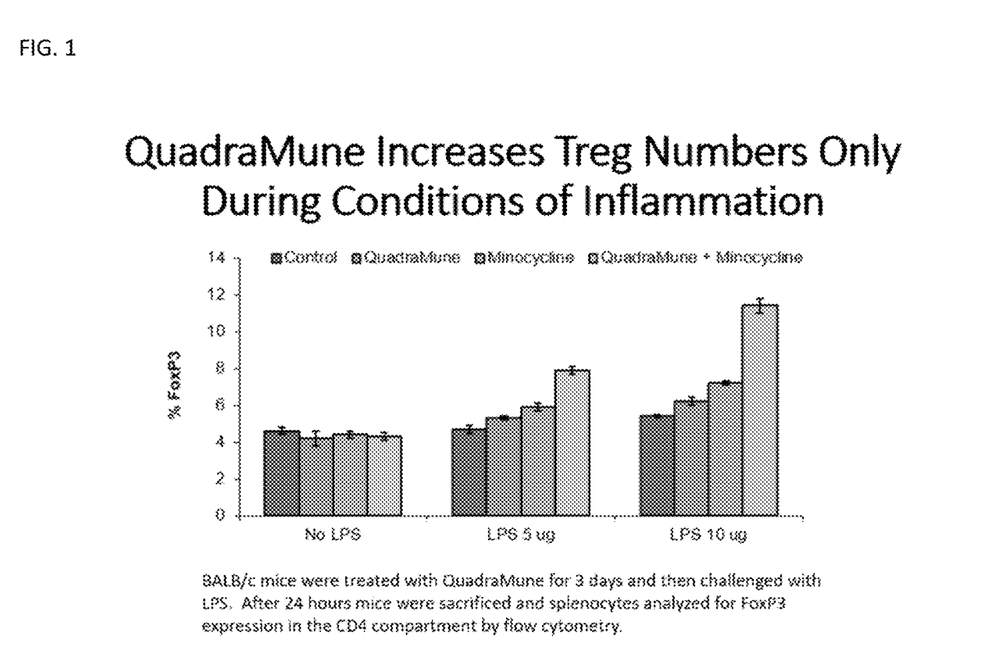
FIG. 1 is a bar graph showing the product containing a) epigallocatechin-3-gallate b) thymoquinone, c) sulforaphane; and d) pterostilbene sold under the trademark QUADRAMUNE® inreases Treg numbers during conditions of inflammation.
Figure 2:
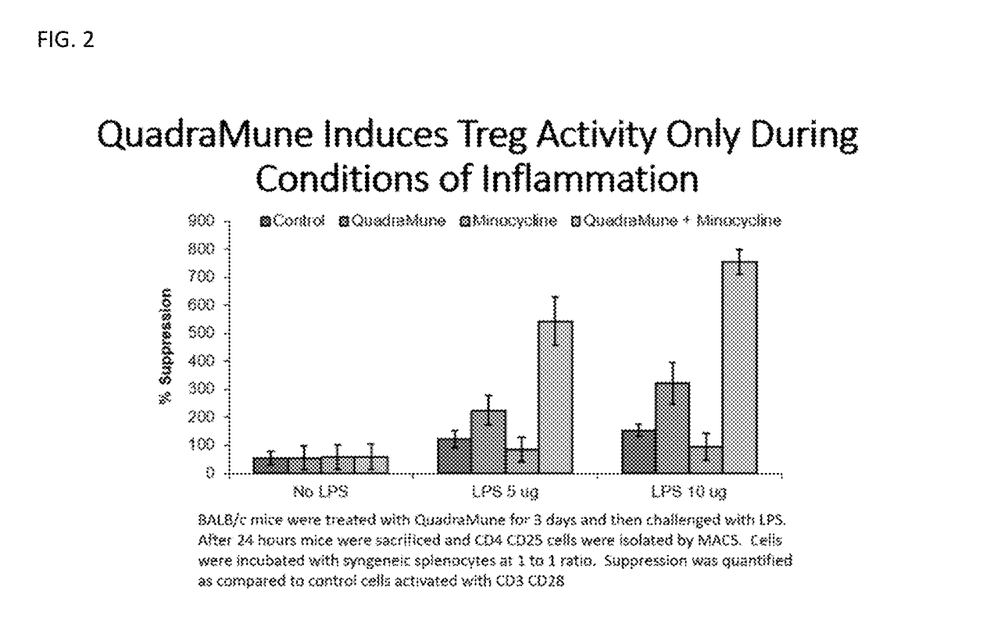
FIG. 2 is a bar graph showing the product containing a) epigallocatechin-3-gallate b) thymoquinone, c) sulforaphane; and d) pterostilbene sold under the trademark QUADRAMUNE® inreases Treg numbers during conditions of inflammation.
Figure 3:
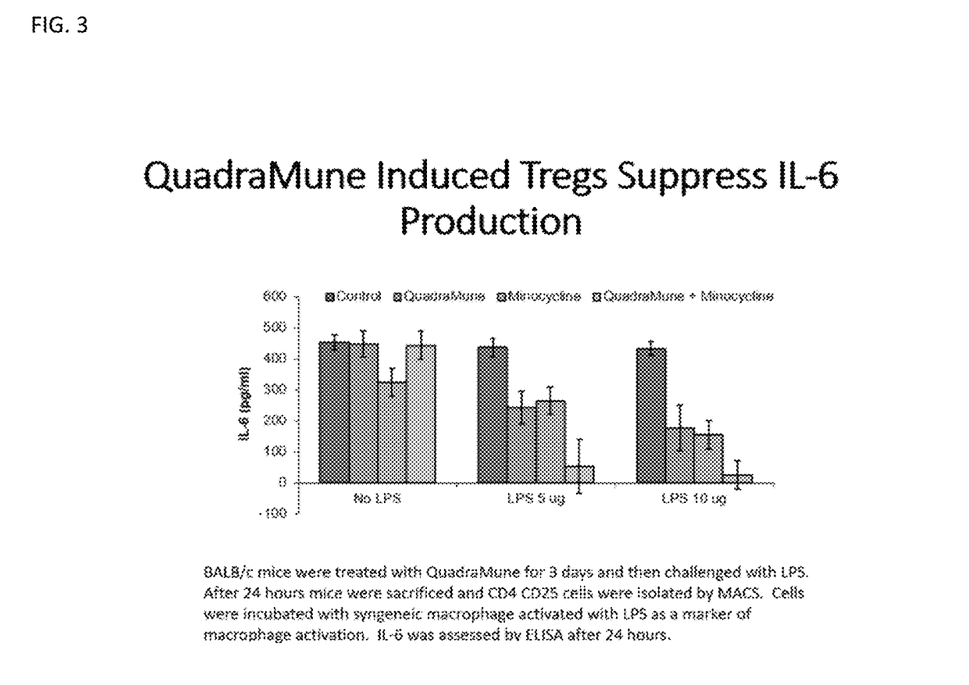
FIG. 3 is a bar graph showing the product containing a) epigallocatechin-3-gallate b) thymoquinone, c) sulforaphane; and d) pterostilbene sold under the trademark QUADRAMUNE® induced Tregs suppress IL-6 production.

The invention provides the unexpected discovery that administration of the product containing a) epigallocatechin-3-gallate b) thymoquinone, c) sulforaphane; and d) pterostilbene sold under the trademark QUADRAMUNE®, leads to generation of Treg cells only under conditions of inflammation. Furthermore, the invention provides that coadministration of the antibiotic minocycline further augments generation of Treg cell numbers, as well as augmentation of activity.

In some embodiment's augmentation of Treg cells is used to decrease neural inflammation. In some embodiments, augmentation of Treg numbers and/or activity is used to treat suicidal ideation.

Pterostilbene (trans-3,5-dimethoxy-4-hydroxystilbene) is a natural polyphenolic compound, primarily found in fruits, such as blueberries, grapes, and tree wood. It has been demonstrated to possess potent antioxidant and anti-inflammatory properties. It is a dimethylated analog of resveratrol which is found in blueberries [13], and is believed to be one of the active ingredients in ancient Indian Medicine [14]. The pterostilbene molecule is structurally similar to resveratrol, the antioxidant found in red wine that has comparable anti-inflammatory, and anticarcinogenic properties; however, pterostilbene exhibits increased bioavailability due to the presence of two methoxy groups which cause it to exhibit increased lipophilic and oral absorption [15-19]. In animal studies, pterostilbene was shown to have 80% bioavailability compared to 20% for resveratrol making it potentially advantageous as a therapeutic agent [15].

We have demonstrated the pterostilbene administered in the form of nanostilbene in cancer patients results in increased NK cell activity, as well as interferon gamma production. Additionally, pterostilbene has shown to inhibit inflammatory cytokines associated with ARDS. For example, studies have demonstrated inhibition of interleukin-1 [20], interleukin-6 [21, 22], interleukin-8 [23], and TNF-alpha [24], by pterostilbene.

It is known that administration of Kalonji increases the potency of the immune system [25, 26]. Specifically, it has been shown that kalonji activates the natural killer cells of the immune system. Natural killer cells, also called NK cells are the body's first line of protection against viruses. It is well known that patients who have low levels of NK cells are very susceptible to viral infections. Kalonji has been demonstrated to increase NK cell activity. In a study published by Dr. Majdalawieh from the American University of Sharjah, Sharjah, United Arab Emirates [27], it was shown that the aqueous extract of *Nigella sativa* significantly enhances NK cytotoxic activity. According to the authors, this supports the idea that NK cell activation by Kalonji can protect not only against viruses, but may also explain why some people report this herb has activity against cancer. It is known that NK cells kill virus infected cells but also kill cancer cells. There are several publications that show that Kalonji has effects against cancer [28-42].

Kalonji suppresses viruses from multiplying. If the virus manages to sneak past the immune system and enters the body, studies have shown that Kalonji, and its active ingredients such as thymoquinone, are able to directly stop viruses, such as coronaviruses and others from multiplying. For example, a study published from University of Gaziantep, in Turkey demonstrated that administration of Kalonji extract to cells infected with coronavirus resulted in suppression of coronavirus multiplication and reduction of pathological protein production [43]. Antiviral activity of Kalonji was demonstrated in other studies, for example, for example, viral hepatitis, and others [44].

Kalonji protects the lungs from pathology. Kalonji was also reported by scholars to possess potent anti-inflammatory effects where its active ingredient thymoquinone suppressed effectively the lipopolysaccharide-induced inflammatory reactions and reduced significantly the concentration of nitric oxide, a marker of inflammation [45]. Moreover, Kalonji has been proven to suppress the pathological processes through blocking the activities of IL-1, IL-6, nuclear factor-KB [46], IL-1 f, cyclooxygenase-1, prostaglandin-E2, prostaglandin-D2 [47], cyclocoxygenase-2, and TNF-α [48] that act as potent inflammatory mediators and were reported to play a major role in the pathogenesis of Coronavirus infection.

Kalonji protects against sepsis/too much inflammation. In peer reviewed study from King Saud University, Riyadh, Saudi Arabia, scientists examined two sets of mice (n=12 per group), with parallel control groups, were acutely treated with thymoquinone (ingredient from Kalonji) intraperitoneal injections of 1.0 and 2.0 mg/kg body weight, and were subsequently challenged with endotoxin Gram-negative bacteria (LPS O111:B4). In another set of experiments, thymoquinone was administered at doses of 0.75 and 1.0 mg/kg/day for three consecutive days prior to sepsis induction with live *Escherichia coli*. Survival of various groups was computed, and renal, hepatic and sepsis markers were quantified. Thymoquinone reduced mortality by 80-90% and improved both renal and hepatic biomarker profiles. The concentrations of IL-1α with 0.75 mg/kg thymoquinone dose was 310.8±70.93 and 428.3±71.32 pg/ml in the 1 mg/kg group as opposed to controls (1187.0±278.64 pg/ml; P<0.05). Likewise, IL-10 levels decreased significantly with 0.75 mg/kg thymoquinone treatment compared to controls (2885.0±553.98 vs. 5505.2±333.96 pg/ml; P<0.01). Mice treated with thymoquinone also exhibited relatively lower levels of TNF-α and IL-2 (P values=0.1817 and 0.0851, respectively). This study gives strength to the potential clinical relevance of thymoquinone in sepsis-related morbidity and mortality reduction and suggests that human studies should be performed [49].

Sulforaphane [1-isothiocyanato-4-(methylsulfinyl)-butane], an isothiocyanate, is a chemopreventive photochemical which is a potent inducer of phase II enzyme involved in the detoxification of xenobiotics [50]. Sulforaphane is produced from the hydrolysis of glucoraphanin, the most abundant glucosinolate found in broccoli, and also present in other Brassicaceae [51]. Numerous studies have reported prevention of cancer [52-56], as well as cancer inhibitory properties of sulforaphane [57-62]. Importantly, this led to studies which demonstrated anti-inflammatory effects of this compound.

One of the fundamental features of inflammation is production of TNF-alpha from monocytic lineage cells. Numerous studies have shown that sulforaphane is capable of suppressing this fundamental initiator of inflammation, in part through blocking NF-kappa B translocation. For example, Lin et al. compared the anti-inflammatory effect of sulforaphane on LPS-stimulated inflammation in primary peritoneal macrophages derived from Nrf2 (+/+) and Nrf2 (−/−) mice. Pretreatment with sulforaphane in Nrf2 (+/+) primary peritoneal macrophages potently inhibited LPS-stimulated mRNA expression, protein expression and production of TNF-alpha, IL-1beta, COX-2 and iNOS. HO-1 expression was significantly augmented in LPS-stimulated Nrf2 (+/+) primary peritoneal macrophages by sulforaphane. Interestingly, the anti-inflammatory effect was attenuated in Nrf2 (−/−) primary peritoneal macrophages. We concluded that SFN exerts its anti-inflammatory activity mainly via activation of Nrf2 in mouse peritoneal macrophages [63]. In a similar study, LPS-challenged macrophages were observed for cytokine production with or without sulforaphane pre-treatment. Macrophages were pre-incubated for 6 h with a wide range of concentrations of SFN (0 to 50 µM), and then treated with LPS for 24 h. Nitric oxide (NO) concentration and gene expression of different inflammatory mediators, i.e., interleukin (IL)-6, tumor necrosis factor (TNF)-α, and IL-1β, were measured. sulforaphane neither directly reacted with cytokines, nor with NO. To understand the mechanisms, the authors performed analyses of the expression of regulatory enzyme inducible nitic oxide synthase (iNOS), the transcription factor NF-E2-related factor 2 (Nrf2), and its enzyme heme-oxygenase (HO)-1. The results revealed that LPS increased significantly the expression of inflammatory cytokines and concentration of NO in non-treated cells. sulforaphane was able to prevent the expression of NO and cytokines through regulating inflammatory enzyme iNOS and activation of Nrf2/HO-1 signal transduction pathway [64]. These data are significant because studies have shown both TNF-alpha but also interleukin-6 are involved in pathology of COVID-19 [65-75]. The utilization of sulforaphane as a substitute for anti-IL-6 antibodies would be more economical and potentially without associated toxicity. Other studies have also demonstrated ability of sulforaphane to suppress IL-6 [76-78]. Interestingly, a clinical study was performed in 40 healthy overweight subjects (ClinicalTrials.gov ID NCT 03390855). Treatment phase consisted on the consumption of broccoli sprouts (30 g/day) during 10 weeks and the follow-up phase of 10 weeks of normal diet without consumption of these broccoli sprouts. Anthropometric parameters as body fat mass, body weight, and BMI were determined. Inflammation status was assessed by measuring levels of TNF-α, IL-6, IL-1β and C-reactive protein. IL-6 levels significantly decreased (mean values from 4.76 pg/mL to 2.11 pg/mL with 70 days of broccoli consumption, $p<0.001$) and during control phase the inflammatory levels were maintained at low grade (mean values from 1.20 pg/mL to 2.66 pg/mL, $p<0.001$). C-reactive protein significantly decreased as well [79].

An additional potential benefit of sulforaphane is its ability to protect lungs against damage. It is known that the major cause of lethality associated with COVID-19 is acute respiratory distress syndrome (ARDS). It was demonstrated that sulforaphane is effective in the endotoxin model of this condition. In one experiments, BALB/c mice were treated with sulforaphane (50 mg/kg) and 3 days later, ARDS was induced by the administration of LPS (5 mg/kg). The results revealed that sulforaphane significantly decreased lactate dehydrogenase (LDH) activity (as shown by LDH assay), the wet-to-dry ratio of the lungs and the serum levels of interleukin-6 (IL-6) and tumor necrosis factor-α (TNF-α) (measured by ELISA), as well as nuclear factor-κB protein expression in mice with LPS-induced ARDS. Moreover, treatment with sulforaphane significantly inhibited prostaglandin E2 (PGE2) production, and cyclooxygenase-2 (COX-2), matrix metalloproteinase-9 (MMP-9) protein expression (as shown by western blot analysis), as well as inducible nitric oxide synthase (iNOS) activity in mice with LPS-induced ALI. Lastly, the researchers reported pretreatment with sulforaphane activated the nuclear factor-E2-related factor 2 (Nrf2)/antioxidant response element (ARE) pathway in the mice with LPS-induced ARDS [80].

EGCG is similar to sulforaphane in that it has been reported to possess cancer preventative properties. This compound has been shown to be one of the top therapeutic ingredients in green tea. It is known from epidemiologic studies that green tea consumption associates with chemoprotective effects against cancer [81-91]. In addition, similarly to sulforaphane, EGCG has been shown to inhibit inflammatory mediators. The first suggestion of this were studies shown suppression of the proinflammatory transcription factor NF-kappa B. In a detailed molecular study, EGCG, a potent antitumor agent with anti-inflammatory and antioxidant properties was shown to inhibit nitric oxide (NO) generation as a marker of activated macrophages. Inhibition of NO production was observed when cells were cotreated with EGCG and LPS. iNOS activity in soluble extracts of lipopolysaccharide-activated macrophages treated with EGCG (5 and 10 microM) for 6-24 hr was significantly lower than that in macrophages without EGCG treatment. Western blot, reverse transcription-polymerase chain reaction, and Northern blot analyses demonstrated that significantly reduced 130-kDa protein and 4.5-kb mRNA levels of iNOS were expressed in lipopolysaccharide-activated macrophages with EGCG compared with those without EGCG. Electrophoretic mobility shift assay indicated that EGCG blocked the activation of nuclear factor-kappaB, a transcription factor necessary for iNOS induction. EGCG also blocked disappearance of inhibitor kappaB from cytosolic fraction. These results suggest that EGCG decreases the activity and protein levels of iNOS by reducing the expression of iNOS mRNA and the reduction could occur through prevention of the binding of nuclear factor-kappaB to the iNOS promoter [92]. Another study supporting ability of EGCG to suppress NF-kappa B examined a model of atherosclerosis in which exposure of macrophage foam cells to TNF-α results in a downregulation of ABCA1 and a decrease in cholesterol efflux to apoA1, which is attenuated by pretreatment with EGCG. Moreover, rather than activating the Liver X receptor (LXR) pathway, inhibition of the TNF-α-induced nuclear factor-κB (NF-κB) activity is detected with EGCG treatment in cells. In order to inhibit the NF-κB activity, EGCG can promote the dissociation of the nuclear factor E2-related factor 2 (Nrf2)-Kelch-like ECH-associated protein 1 (Keap1) complex; when the released Nrf2 translocates to the nucleus and activates the transcription of genes containing an ARE element inhibition of NF-κB occurs and Keap1 is separated from the complex to directly interact with IKKβ and thus represses NF-κB function [93].

The anti-inflammatory effects of EGCG can be seen in the ability of this compound to potently inhibit IL-6, the COVID-19 associated cytokine, in a variety of inflammatory settings. For example, in a cardiac infarct model, rats were subjected to myocardial ischemia (30 min) and reperfusion (up to 2 h). Rats were treated with EGCG (10 mg/kg intravenously) or with vehicle at the end of the ischemia period followed by a continuous infusion (EGCG 10 mg/kg/h) during the reperfusion period. In vehicle-treated rats, extensive myocardial injury was associated with tissue neutrophil infiltration as evaluated by myeloperoxidase activity, and elevated levels of plasma creatine phosphokinase. Vehicle-treated rats also demonstrated increased plasma levels of interleukin-6. These events were associated with cytosol degradation of inhibitor kappaB-alpha, activation of IkappaB kinase, phosphorylation of c-Jun, and subsequent activation of nuclear factor-kappaB and activator protein-1 in the infarcted heart. In vivo treatment with EGCG reduced myocardial damage and myeloperoxidase activity. Plasma IL-6 and creatine phosphokinase levels were decreased after EGCG administration. This beneficial effect of EGCG was associated with reduction of nuclear factor-kB and activator protein-1 DNA binding [94]. In an inflammatory model of ulcerative colitis (UC) mice were randomly divided into four groups: Normal control, model (MD), 50 mg/kg/day EGCG treatment and 100 mg/kg/day EGCG treatment. The daily disease activity index (DAI) of the mice was recorded, changes in the organizational structure of the colon were observed and the spleen index (SI) was measured. In addition, levels of interleukin (IL)-6, IL-10, IL-17 and transforming growth factor (TGF)-β1 in the plasma and hypoxia-inducible factor (HIF)-1α and signal transducer and activator of transcription (STAT) 3 protein expression in colon tissues were evaluated. Compared with the MD group, the mice in the two EGCG treatment groups exhibited decreased DAIs and SIs and an attenuation in the colonic tissue erosion. EGCG could reduce the release of IL-6 and IL-17 and regulate the mouse splenic regulatory T-cell (Treg)/T helper 17 cell (Th17) ratio, while increasing the plasma levels of IL-10 and TGF-β1 and decreasing the HIF-1α and STAT3 protein expression in the colon. The experiments confirmed that EGCG treated mice with experimental colitis by inhibiting the release of IL-6 and regulating the body Treg/Th17 balance [95].

In patients with COVID-19, the ARDS associated with fatality resembles septic shock in many aspects, including DIC, fever, vascular leakage, and systemic inflammation. Wheeler et al. induced polymicrobialsepsis in male Sprague-Dawley rats (hemodynamic study) and C57BL6 mice (mortality study) via cecal ligation and double puncture (CL2P). Rodents were treated with either EGCG (10 mg/kg intraperitoneally) or vehicle at 1 and 6 h after CL2P and every 12 h thereafter. In the hemodynamic study, mean arterial blood pressure was monitored for 18 h, and rats were killed at 3, 6, and 18 h after CL2P. In the mortality study, survival was monitored for 72 h after CL2P in mice. In vehicle-treated rodents, CL2P was associated with profound hypotension and greater than 80% mortality rate. Epigallocatechin-3-gallate treatment significantly improved both the hypotension and survival [96]. A subsequent study by Li et al. showed intraperitoneal administration of EGCG protected mice against lethal endotoxemia, and rescued mice from lethal sepsis even when the first dose was given 24 hours after cecal ligation and puncture. The therapeutic effects were partly attributable to: 1) attenuation of systemic accumulation of proinflammatory mediator (e.g., HMGB1) and surrogate marker (e.g., IL-6 and KC) of lethal sepsis; and 2) suppression of HMGB1-mediated inflammatory responses by preventing clustering of exogenous HMGB1 on macrophage cell surface [97].

Finally, in a lung study mice were treated with EGCG (10 mg/kg) intraperitoneally (ip) 1 h before LPS injection (10 mg/kg, ip). The results showed that EGCG attenuated LPS-induced ARDS as it decreased the changes in blood gases and reduced the histological lesions, wet-to-dry weight ratios, and myeloperoxidase (MPO) activity. In addition, EGCG significantly decreased the expression of proinflammatory cytokines tumor necrosis factor (TNF)-α, interleukin (IL)-1f, and IL-6 in the lung, serum, and bronchoalveolar lavage fluid, and alleviated the expression of TLR-4, MyD88, TRIF, and p-p65 in the lung tissue. In addition, it increased the expression of IκB-α and had no influence on the expression of p65. Collectively, these results demonstrated the protective effects of EGCG against LPS-induced ARDS in mice through its anti-inflammatory effect that may be attributed to the suppression of the activation of TLR 4-dependent NF-κB signaling pathways [98].

Example 1 Augmentation of Number and Function of T regulatory Cells by QUADRAMUNE®

Mice given the product containing a) epigallocatechin-3-gallate b) thymoquinone, c) sulforaphane; and d) pterostilbene sold under the trademark QUADRAMUNE® components for 3 days prior to LPS challenge. BALB/c mice given LPS challenge or no LPS challenge.LPS Challenge is to replicate conditions of inflammation. Mice sacrificed 24 hours later and number and activity of T regulatory cells was quantified. Number of T regulatory cells by FoxP3 cell quantification. Activity of T regulatory cells assessed by ability to inhibit anti-CD3 anti-CD28 activated T cells.

REFERENCES

1. Formby B, Shao T: T cell vaccination against autoimmune diabetes in nonobese diabetic mice. *Ann Clin Lab Sci* 1993, 23(2):137-147.
2. Singer S M, Tisch R, Yang X D, McDevitt H O: An Abd transgene prevents diabetes in nonobese diabetic mice by inducing regulatory T cells. *Proc Natl Acad Sci USA* 1993, 90(20):9566-9570.
3. Sempe P, Richard M F, Bach J F, Boitard C: Evidence of CD4+ regulatory T cells in the non-obese diabetic male mouse. *Diabetologia* 1994, 37(4):337-343.
4. Bergerot I, Fabien N, Maguer V, Thivolet C: Oral administration of human insulin to NOD mice generates CD4+ T cells that suppress adoptive transfer of diabetes. *J Autoimmun* 1994,7(5):655-663.
5. Whalen B J, Greiner D L, Mordes J P, Rossini A A: Adoptive transfer of autoimmune diabetes mellitus to athymic rats: synergy of CD4+ and CD8+ T cells and prevention by RT6+ T cells. *J Autoimmun* 1994, 7(6): 819-831.
6. Sobel D O, Yankelevich B, Goyal D, Nelson D, Mazumder A: The B-subunit of cholera toxin induces immunoregulatory cells and prevents diabetes in the NOD mouse. *Diabetes* 1998, 47(2):186-191.
7. Tisch R, Liblau R S, Yang X D, Liblau P, McDevitt H O: Induction of GAD65-specific regulatory T-cells inhibits ongoing autoimmune diabetes in nonobese diabetic mice. *Diabetes* 1998, 47(6):894-899.
8. Seddon B, Mason D: Peripheral autoantigen induces regulatory T cells that prevent autoimmunity. *J Exp Med* 1999, 189(5):877-882.
9. Bergerot I, Arreaza G A, Cameron M J, Burdick M D, Strieter R M, Chensue S W, Chakrabarti S, Delovitch T L: Insulin B-chain reactive CD4+ regulatory T-cells induced by oral insulin treatment protect from type 1 diabetes by blocking the cytokine secretion and pancreatic infiltration of diabetogenic effector T-cells. *Diabetes* 1999, 48(9): 1720-1729.
10. Stephens L A, Mason D: CD25 is a marker for CD4+ thymocytes that prevent autoimmune diabetes in rats, but peripheral T cells with this function are found in both CD25+ and CD25-subpopulations. *J Immunol* 2000, 165 (6):3105-3110.
11. Treschow A P, Backlund J, Holmdahl R, Issazadeh-Navikas S: Intrinsic tolerance in autologous collagen-induced arthritis is generated by CD152-dependent CD4+ suppressor cells. *J Immunol* 2005, 174(11):6742-6750.

12. Duffy S S, Keating B A, Moalem-Taylor G: Adoptive Transfer of Regulatory T Cells as a Promising Immunotherapy for the Treatment of Multiple Sclerosis. *Front Neurosci* 2019, 13:1107.
13. McCormack D, McFadden D: A review of pterostilbene antioxidant activity and disease modification. *Oxid Med Cell Longev* 2013, 2013:575482.
14. Paul B, Masih I, Deopujari J, Charpentier C: Occurrence of resveratrol and pterostilbene in age-old darakchasava, an ayurvedic medicine from India. *J Ethnopharmacol* 1999, 68(1-3):71-76.
15. Kapetanovic I M, Muzzio M, Huang Z, Thompson T N, McCormick D L: Pharmacokinetics, oral bioavailability, and metabolic profile of resveratrol and its dimethylether analog, pterostilbene, in rats. *Cancer Chemother Pharmacol* 2011, 68(3):593-601.
16. Perecko T, Drabikova K, Rackova L, Ciz M, Podborska M, Lojek A, Harmatha J, Smidrkal J, Nosal R, Jancinova V: Molecular targets of the natural antioxidant pterostilbene: effect on protein kinase C, caspase-3 and apoptosis in human neutrophils in vitro. *Neuro Endocrinol Lett* 2010, 31 Suppl 2:84-90.
17. Stivala L A, Savio M, Carafoli F, Perucca P, Bianchi L, Maga G, Forti L, Pagnoni U M, Albini A, Prosperi E et al: Specific structural determinants are responsible for the antioxidant activity and the cell cycle effects of resveratrol. *J Biol Chem* 2001, 276(25):22586-22594.
18. Athar M, Back J H, Tang X, Kim K H, Kopelovich L, Bickers D R, Kim A L: Resveratrol: a review of preclinical studies for human cancer prevention. *Toxicol Appl Pharmacol* 2007, 224(3):274-283.
19. Bishayee A: Cancer prevention and treatment with resveratrol: from rodent studies to clinical trials. *Cancer Prev Res* (Phila) 2009, 2(5):409-418.
20. Hsu C L, Lin Y J, Ho C T, Yen G C: The inhibitory effect of pterostilbene on inflammatory responses during the interaction of 3T3-L1 adipocytes and RAW 264.7 macrophages. *J Agric Food Chem* 2013, 61(3):602-610.
21. McCormack D, McDonald D, McFadden D: Pterostilbene ameliorates tumor necrosis factor alpha-induced pancreatitis in vitro. *J Surg Res* 2012, 178(1):28-32.
22. Erasalo H, Hamalainen M, Leppanen T, Maki-Opas I, Laavola M, Haavikko R, Yli-Kauhaluomaj, Moilanen E: Natural Stilbenoids Have Anti-Inflammatory Properties in Vivo and Down-Regulate the Production of Inflammatory Mediators NO, IL6, and MCP1 Possibly in a PI3K/Akt-Dependent Manner. *J Nat Prod* 2018, 81(5):1131-1142.
23. Allijn I E, Vaessen S F, Quarles van Ufford L C, Beukelman K J, de Winther M P, Storm G, Schiffelers R M: Head-to-Head Comparison of Anti-Inflammatory Performance of Known Natural Products In Vitro. *PLoS One* 2016, 11(5):e0155325.
24. Meng X L, Yang J Y, Chen G L, Wang L H, Zhang L J, Wang S, Li J, Wu C F: Effects of resveratrol and its derivatives on lipopolysaccharide-induced microglial activation and their structure-activity relationships. *Chem Biol Interact* 2008, 174(1):51-59.
25. Swamy S M, Tan B K: Cytotoxic and immunopotentiating effects of ethanolic extract of *Nigella sativa* L. seeds. *J Ethnopharmacol* 2000, 70(1):1-7.
26. Salem M L, Alenzi F Q, Attia W Y: Thymoquinone, the active ingredient of *Nigella sativa* seeds, enhances survival and activity of antigen-specific CD8-positive T cells in vitro. *Br J Biomed Sci* 2011, 68(3):131-137.
27. Majdalawieh A F, Hmaidan R, Carr R I: *Nigella sativa* modulates splenocyte proliferation, Th1/Th2 cytokine profile, macrophage function and NK anti-tumor activity. *J Ethnopharmacol* 2010, 131(2):268-275.
28. Salomi M J, Panikkar K R, Kesavan M, Donata K, Sr., Rajagopalan K: Anti-cancer activity of *Nigella sativa*. *Anc Sci Life* 1989, 8(3-4):262-266.
29. Salomi N J, Nair S C, Jayawardhanan K K, Varghese C D, Panikkar K R: Antitumour principles from *Nigella sativa* seeds. *Cancer Lett* 1992, 63(1):41-46.
30. Ait Mbarek L, Ait Mouse H, Elabbadi N, Bensalah M, Gamouh A, Aboufatima R, Benharref A, Chait A, Kamal M, Dalal A et al: Anti-tumor properties of blackseed (*Nigella sativa* L.) extracts. *Braz J Med Biol Res* 2007, 40(6):839-847.
31. Amara A A, El-Masry M H, Bogdady H H: Plant crude extracts could be the solution: extracts showing in vivo antitumorigenic activity. *Pak J Pharm Sci* 2008, 21(2):159-171.
32. Banerjee S, Padhye S, Azmi A, Wang Z, Philip P A, Kucuk O, Sarkar F H, Mohammad R M: Review on molecular and therapeutic potential of thymoquinone in cancer. *Nutr Cancer* 2010, 62(7):938-946.
33. Khan M A, Chen H C, Tania M, Zhang D Z: Anticancer activities of *Nigella sativa* (black cumin). *Afr J Tradit Complement Altern Med* 2011, 8(5 Suppl):226-232.
34. Woo C C, Kumar A P, Sethi G, Tan K H: Thymoquinone: potential cure for inflammatory disorders and cancer. *Biochem Pharmacol* 2012, 83(4):443-451.
35. Lei X, Lv X, Liu M, Yang Z, Ji M, Guo X, Dong W: Thymoquinone inhibits growth and augments 5-fluorouracil-induced apoptosis in gastric cancer cells both in vitro and in vivo. *Biochem Biophys Res Commun* 2012, 417 (2):864-868.
36. Linjawi S A, Khalil W K, Hassanane M M, Ahmed E S: Evaluation of the protective effect of *Nigella sativa* extract and its primary active component thymoquinone against DMBA-induced breast cancer in female rats. *Arch Med Sci* 2015, 11(1):220-229.
37. Majdalawieh A F, Fayyad M W: Recent advances on the anti-cancer properties of *Nigella sativa*, a widely used food additive. *J Ayurveda Integr Med* 2016, 7(3):173-180.
38. Majdalawieh A F, Fayyad M W, Nasrallah G K: Anticancer properties and mechanisms of action of thymoquinone, the major active ingredient of *Nigella sativa*. *Crit Rev Food Sci Nutr* 2017, 57(18):3911-3928.
39. Mostofa A G M, Hossain M K, Basak D, Bin Sayeed M S: Thymoquinone as a Potential Adjuvant Therapy for Cancer Treatment: Evidence from Preclinical Studies. *Front Pharmacol* 2017, 8:295.
40. Asaduzzaman Khan M, Tania M, Fu S, Fu J: Thymoquinone, as an anticancer molecule: from basic research to clinical investigation. *Oncotarget* 2017, 8(31):51907-51919.
41. Imran M, Rauf A, Khan I A, Shahbaz M, Qaisrani T B, Fatmawati S, Abu-Izneid T, Imran A, Rahman K U, Gondal T A: Thymoquinone: A novel strategy to combat cancer: A review. *Biomed Pharmacother* 2018, 106:390-402.
42. Zhang Y, Fan Y, Huang S, Wang G, Han R, Lei F, Luo A, Jing X, Zhao L, Gu S et al: Thymoquinone inhibits the metastasis of renal cell cancer cells by inducing autophagy via AMPK/mTOR signaling pathway. *Cancer Sci* 2018, 109(12):3865-3873.
43. Ulasli M, Gurses S A, Bayraktar R, Yumrutas O, Oztuzcu S, Igci M, Igci Y Z, Cakmak E A, Arslan A: The effects of *Nigella sativa* (Ns), *Anthemis hyalina* (Ah) and *Citrus* sinensis (Cs) extracts on the replication of coronavirus and the expression of TRP genes family. *Mol Biol Rep* 2014, 41(3):1703-1711.
44. Ahmad A, Husain A, Mujeeb M, Khan S A, Najmi A K, Siddique N A, Damanhouri Z A, Anwar F: A review on therapeutic potential of *Nigella sativa*: A miracle herb. *Asian Pac J Trop Biomed* 2013, 3(5):337-352.
45. Alemi M, Sabouni F, Sanjarian F, Haghbeen K, Ansari S: Anti-inflammatory effect of seeds and callus of *Nigella sativa* L. extracts on mix glial cells with regard to their thymoquinone content. *AAPS Pharm Sci Tech* 2013, 14(1):160-167.
46. Shuid A N, Mohamed N, Mohamed I N, Othman F, Suhaimi F, Mohd Ramli E S, Muhammad N, Soelaiman I N: *Nigella sativa*: A Potential Antiosteoporotic Agent. *Evid Based Complement Alternat Med* 2012, 2012: 696230.
47. El Mezayen R, El Gazzar M, Nicolls M R, Marecki J C, Dreskin S C, Nomiyama H: Effect of thymoquinone on cyclooxygenase expression and prostaglandin production in a mouse model of allergic airway inflammation. *Immunol Lett* 2006, 106(1):72-81.
48. Chehl N, Chipitsyna G, Gong Q, Yeo C J, Arafat H A: Anti-inflammatory effects of the *Nigella sativa* seed extract, thymoquinone, in pancreatic cancer cells. *HPB* (Oxford) 2009, 11(5):373-381.
49. Alkharfy K M, Al-Daghri N M, Al-Attas O S, Alokail M S: The protective effect of thymoquinone against sepsis syndrome morbidity and mortality in mice. *Int Immunopharmacol* 2011, 11(2):250-254.
50. Shen G, Khor T O, Hu R, Yu S, Nair S, Ho C T, Reddy B S, Huang M T, Newmark H L, Kong A N: Chemoprevention of familial adenomatous polyposis by natural dietary compounds sulforaphane and dibenzoylmethane alone and in combination in ApcMin/+ mouse. *Cancer Res* 2007, 67(20):9937-9944.
51. Zambrano V, Bustos R, Mahn A: Insights about stabilization of sulforaphane through microencapsulation. Heliyon 2019, 5(11):e02951.
52. Steinkellner H, Rabot S, Freywald C, Nobis E, Scharf G, Chabicovsky M, Knasmuller S, Kassie F: Effects of cruciferous vegetables and their constituents on drug metabolizing enzymes involved in the bioactivation of DNA-reactive dietary carcinogens. *Mutat Res* 2001, 480-481:285-297.
53. Fahey J W, Zhang Y, Talalay P: Broccoli sprouts: an exceptionally rich source of inducers of enzymes that protect against chemical carcinogens. *Proc Nat Acad Sci USA* 1997, 94(19):10367-10372.
54. Solowiej E, Kasprzycka-Guttman T, Fiedor P, Rowinski W: Chemoprevention of cancerogenesis—the role of sulforaphane. *Acta Pol Pharm* 2003, 60(1):97-100.
55. Gills J J, Jeffery E H, Matusheski N V, Moon R C, Lantvit D D, Pezzuto J M: Sulforaphane prevents mouse skin tumorigenesis during the stage of promotion. *Cancer Lett* 2006,236(1):72-79.
56. Myzak M C, Dashwood W M, Omer G A, Ho E, Dashwood R H: Sulforaphane inhibits histonedeacetylase in vivo and suppresses tumorigenesis in Apc-minus mice. *FASEB J* 2006, 20(3):506-508.
57. Singh A V, Xiao D, Lew K L, Dhir R, Singh S V: Sulforaphane induces caspase-mediated apoptosis in cultured PC-3 human prostate cancer cells and retards growth of PC-3 xenografts in vivo. *Carcinogenesis* 2004, 25(1):83-90.
58. Wang L, Liu D, Ahmed T, Chung F L, Conaway C, Chiao J W: Targeting cell cycle machinery as a molecular mechanism of sulforaphane in prostate cancer prevention. *Int J Oncol* 2004,24(1):187-192.
59. Pham N A, Jacobberger J W, Schimmer A D, Cao P, Gronda M, Hedley D W: The dietary isothiocyanate sulforaphane targets pathways of apoptosis, cell cycle arrest, and oxidative stress in human pancreatic cancer cells and inhibits tumor growth in severe combined immunodeficient mice. *Mol Cancer Ther* 2004, 3(10): 1239-1248.
60. Thejass P, Kuttan G: Antimetastatic activity of Sulforaphane. *Life Sci* 2006, 78(26):3043-3050.
61. Fimognari C, Hrelia P: Sulforaphane as a promising molecule for fighting cancer. *Mutat Res* 2007, 635(2-3): 90-104.
62. Li Y, Zhang T, Korkaya H, Liu S, Lee H F, Newman B, Yu Y, Clouthier S G, Schwartz S J, Wicha M S et al: Sulforaphane, a dietary component of broccoli/broccoli sprouts, inhibits breast cancer stem cells. *Clin Cancer Res* 2010, 16(9):2580-2590.
63. Lin W, Wu R T, Wu T, Khor T O, Wang H, Kong A N: Sulforaphane suppressed LPS-induced inflammation in mouse peritoneal macrophages through Nrf2 dependent pathway. *Biochem Pharmacol* 2008, 76(8):967-973.
64. Ruhee R T, Ma S, Suzuki K: Sulforaphane Protects Cells against Lipopolysaccharide-Stimulated Inflammation in Murine Macrophages. Antioxidants (Basel) 2019, 8(12).
65. Xu X, Han M, Li T, Sun W, Wang D, Fu B, Zhou Y, Zheng X, Yang Y, Li X et al: Effective treatment of severe COVID-19 patients with tocilizumab. *Proc Natl Acad Sci USA* 2020.
66. Liu F, Li L, Xu M, Wu J, Luo D, Zhu Y, Li B, Song X, Zhou X: Prognostic value of interleukin-6, C-reactive protein, and procalcitonin in patients with COVID-19. *J Clin Virol* 2020, 127:104370.
67. Aziz M, Fatima R, Assaly R: Elevated Interleukin-6 and Severe COVID-19: A Meta-Analysis. *J Med Virol* 2020.
68. Chen X, Zhao B, Qu Y, Chen Y, Xiong J, Feng Y, Men D, Huang Q, Liu Y, Yang B et al: Detectable serum SARS-CoV-2 viral load (RNAaemia) is closely correlated with drastically elevated interleukin 6 (IL-6) level in critically ill COVID-19 patients. *Clin Infect Dis* 2020.
69. Zhang C, Wu Z, Li J W, Zhao H, Wang G Q: The cytokine release syndrome (CRS) of severe COVID-19 and Interleukin-6 receptor (IL-6R) antagonist Tocilizumab may be the key to reduce the mortality. *Int J Antimicrob Agents* 2020:105954.
70. Zhang X, Song K, Tong F, Fei M, Guo H, Lu Z, Wang J, Zheng C: First case of COVID-19 in a patient with multiple myeloma successfully treated with tocilizumab. *Blood Adv* 2020, 4(7):1307-1310.
71. McGonagle D, Sharif K, O'Regan A, Bridgewood C: The Role of Cytokines including Interleukin-6 in COVID-19 induced Pneumonia and Macrophage Activation Syndrome-Like Disease. *Autoimmun Rev* 2020:102537.
72. Luo P, Liu Y, Qiu L, Liu X, Liu D, Li J: Tocilizumab treatment in COVID-19: A single center experience. *J Med Virol* 2020.
73. Ulhaq Z S, Soraya G V: Interleukin-6 as a potential biomarker of COVID-19 progression. *Med Mal Infect* 2020.
74. Fu B, Xu X, Wei H: Why tocilizumab could be an effective treatment for severe COVID-19? *J Transl Med* 2020, 18(1):164.
75. Liu B, Li M, Zhou Z, Guan X, Xiang Y: Can we use interleukin-6 (IL-6) blockade for coronavirus disease 2019 (COVID-19)-induced cytokine release syndrome (CRS)? *J Autoimmun* 2020:102452.

76. Eren E, Tufekci K U, Isci K B, Tastan B, Gene K, Gene S: Sulforaphane Inhibits Lipopolysaccharide-Induced Inflammation, Cytotoxicity, Oxidative Stress, and miR-155 Expression and Switches to Mox Phenotype through Activating Extracellular Signal-Regulated Kinase 1/2-Nuclear Factor Erythroid 2-Related Factor 2/Antioxidant Response Element Pathway in Murine Microglial Cells. *Front Immunol* 2018, 9:36.

77. Ma T, Zhu D, Chen D, Zhang Q, Dong H, Wu W, Lu H, Wu G: Sulforaphane, a Natural Isothiocyanate Compound, Improves Cardiac Function and Remodeling by Inhibiting Oxidative Stress and Inflammation in a Rabbit Model of Chronic Heart Failure. *Med Sci Monit* 2018, 24:1473-1483.

78. Liu H, Zimmerman A W, Singh K, Connors S L, Diggins E, Stephenson K K, Dinkova-Kostova A T, Fahey J W: Biomarker Exploration in Human Peripheral Blood Mononuclear Cells for Monitoring Sulforaphane Treatment Responses in Autism Spectrum Disorder. *Sci Rep* 2020, 10(1):5822.

79. Lopez-Chillon M T, Carazo-Diaz C, Prieto-Merino D, Zafrilla P, Moreno D A, Villano D: Effects of long-term consumption of broccoli sprouts on inflammatory markers in overweight subjects. *Clin Nutr* 2019, 38(2):745-752.

80. Qi T, Xu F, Yan X, Li S, Li H: Sulforaphane exerts anti-inflammatory effects against lipopolysaccharide-induced acute lung injury in mice through the Nrf2/ARE pathway. *Int J Mol Med* 2016, 37(1):182-188.

81. Dashwood R H, Xu M, Hernaez J F, Hasaniya N, Youn K, Razzuk A: Cancer chemopreventive mechanisms of tea against heterocyclic amine mutagens from cooked meat. *Proc Soc Exp Biol Med* 1999, 220(4):239-243.

82. Brown M D: Green tea (*Camellia sinensis*) extract and its possible role in the prevention of cancer. *Altern Med Rev* 1999, 4(5):360-370.

83. Banerjee S, Manna S, Mukherjee S, Pal D, Panda C K, Das S: Black tea polyphenols restrict benzopyrene-induced mouse lung cancer progression through inhibition of Cox-2 and induction of caspase-3 expression. *Asian Pac J Cancer Prev* 2006, 7(4):661-666.

84. Shimizu M, Shirakami Y, Moriwaki H: Targeting receptor tyrosine kinases for chemoprevention by green tea catechin, EGCG. *Int J Mol Sci* 2008, 9(6):1034-1049.

85. Johnson J J, Bailey H H, Mukhtar H: Green tea polyphenols for prostate cancer chemoprevention: a translational perspective. *Phytomedicine* 2010, 17(1):3-3.

86. Kim J W, Amin A R, Shin D M: Chemoprevention of head and neck cancer with green tea polyphenols. *Cancer Prev Res* (Phila) 2010, 3(8):900-909.

87. Henning S M, Wang P, Heber D: Chemopreventive effects of tea in prostate cancer: green tea versus black tea. *Mol Nutr Food Res* 2011, 55(6):905-920.

88. Du G J, Zhang Z, Wen X D, Yu C, Calway T, Yuan C S, Wang C Z: Epigallocatechin Gallate (EGCG) is the most effective cancer chemopreventive polyphenol in green tea. *Nutrients* 2012, 4(11):1679-1691.

89. Henning S M, Wang P, Abgaryan N, Vicinanza R, de Oliveira D M, Zhang Y, Lee R P, Carpenter C L, Aronson W J, Heber D: Phenolic acid concentrations in plasma and urine from men consuming green or black tea and potential chemopreventive properties for colon cancer. *Mol Nutr Food Res* 2013, 57(3):483-493.

90. Schramm L: Going Green: The Role of the Green Tea Component EGCG in Chemoprevention. *J Carcinog Mutagen* 2013, 4(142):1000142.

91. Rahmani A H, Al Shabrmi F M, Allemailem K S, Aly S M, Khan M A: Implications of Green Tea and Its Constituents in the Prevention of Cancer via the Modulation of Cell Signalling Pathway. *Biomed Res Int* 2015, 2015:925640.

92. Lin Y L, Lin J K: (-)-Epigallocatechin-3-gallate blocks the induction of nitric oxide synthase by down-regulating lipopolysaccharide-induced activity of transcription factor nuclear factor-kappaB. *Mol Pharmacol* 1997, 52(3):465-472.

93. Jiang J, Mo Z C, Yin K, Zhao G J, Lv Y C, Ouyang X P, Jiang Z S, Fu Y, Tang C K: Epigallocatechin-3-gallate prevents TNF-alpha-induced NF-kappaB activation thereby upregulating ABCA1 via the Nrf2/Keap1 pathway in macrophage foam cells. *Int J Mol Med* 2012, 29(5):946-956.

94. Aneja R, Hake P W, Burroughs T J, Denenberg A G, Wong H R, Zingarelli B: Epigallocatechin, a green tea polyphenol, attenuates myocardial ischemia reperfusion injury in rats. *Mol Med* 2004, 10(1-6):55-62.

95. Xu Z, Wei C, Zhang R U, Yao J, Zhang D, Wang L: Epigallocatechin-3-gallate-induced inhibition of interleukin-6 release and adjustment of the regulatory T/T helper 17 cell balance in the treatment of colitis in mice. *Exp Ther Med* 2015, 10(6):2231-2238.

96. Wheeler D S, Lahni P M, Hake P W, Denenberg A G, Wong H R, Snead C, Catravas J D, Zingarelli B: The green tea polyphenol epigallocatechin-3-gallate improves systemic hemodynamics and survival in rodent models of polymicrobial sepsis. *Shock* 2007, 28(3):353-359.

97. Li W, Ashok M, Li J, Yang H, Sama A E, Wang H: A major ingredient of green tea rescues mice from lethal sepsis partly by inhibiting HMGB1. *PLoS One* 2007, 2(11):e1153.

98. Wang J, Fan S M, Zhang J: Epigallocatechin-3-gallate ameliorates lipopolysaccharide-induced acute lung injury by suppression of TLR4/NF-kappaB signaling activation. *Braz J Med Biol Res* 2019, 52(7):e8092.

The invention claimed is:

1. A method of stimulating production of T regulatory cells in a mammal comprising the steps of: a) selecting a mammal in need of therapy; b) administering to said mammal a therapeutic combination comprising of: a) epigallocatechin-3-gallate or a green tea extract containing epigallocatechin-3-gallate; b) pterostilbene or a blueberry extract containing pterostilbene; c) thymoquinone or a *Nigella sativa* extract containing thymoquinone; d) sulforaphane or a broccoli extract containing sulforaphane and e) minocycline.

2. The method of claim 1, wherein said T regulatory cells are stimulated in a patient possessing deficient numbers and/or activity of said T regulatory cells.

3. The method of claim 2, wherein said numbers of T regulatory cells are quantified by assessing number of cells expressing FoxP3.

4. The method of claim 2, wherein said activity of said T regulatory cells is quantified by assessing ability of said T regulatory cells to suppress proliferation of T cell receptor stimulated CD4 T cells.

5. The method of claim 4, wherein proliferation of said CD4 or CD8 T cells is induced by exposure to a mitogen.

6. The method of claim 2, wherein said activity of said T regulatory cells is quantified by assessing ability of said T regulatory cells to suppress proliferation of T cell receptor stimulated CD8 T cells.

7. The method of claim 1, wherein said T regulatory cells reduce neuroinflammation.

8. The method of claim 7, wherein said neuroinflammation is associated with enhanced production of TNF-alpha as compared to an age-matched control.

9. The method of claim 8, wherein said TNF-alpha is measured in the peripheral blood.

10. The method of claim 8, wherein said TNF-alpha is measured in the cerebral spinal fluid.

11. A method of reducing suicidal ideations comprising the steps of: a) selecting a mammal in need of therapy; b) administering to said mammal a therapeutic combination comprising of: a) epigallocatechin-3-gallate or a green tea extract containing epigallocatechin-3-gallate; b) pterostilbene or a blueberry extract containing pterostilbene; c) thymoquinone or a *Nigella sativa* extract containing thymoquinone; d) sulforaphane or a broccoli extract containing sulforaphane and e) minocycline.

12. The method of claim 11, wherein said suicidal ideation is assessed using one or more methods selected from the group consisting of: a) Campbell Score; b) SAD PERSONS scale; c) Manchester Self Harm Rule; d) Sodersjukhuset Self Harm Rule; and e) Beck Hopelessness Scale.

13. The method of claim 11, wherein said minocycline is administered between 10 mg/day to 2 grams/day.

14. The method of claim 11, wherein said minocycline is administered between 10 mg/day to 700 milligrams/day.

15. The method of claim 11, wherein said minocycline is administered between 10 mg/day to 400 milligrams/day.

16. The method of claim 11, where said therapeutic composition is administered at a sufficient dose and frequency to increase production of interleukin 10 from peripheral blood mononuclear cells.

17. The method of claim 11, where said therapeutic composition is administered at a sufficient dose and frequency to increase production of interleukin 10 from microglial cells.

18. The method of claim 11, where said therapeutic composition is administered at a sufficient dose and frequency to decrease production of interleukin 6 from peripheral blood mononuclear cells.

19. The method of claim 11, where said therapeutic composition is administered at a sufficient dose and frequency to increase production of interleukin 6 from microglial cells.

\* \* \* \* \*